United States Patent [19]

Breslow

[11] 4,240,971
[45] Dec. 23, 1980

[54] EPOXY-SULFONYLAZIDE COMPOUNDS

[75] Inventor: David S. Breslow, Wilmington, Del.

[73] Assignee: Hercules Incorporated, Wilmington, Del.

[21] Appl. No.: 645,761

[22] Filed: Dec. 31, 1975

Related U.S. Application Data

[60] Continuation-in-part of Ser. No. 483,471, Jun. 26, 1974, abandoned, which is a continuation-in-part of Ser. No. 301,003, Oct. 26, 1972, abandoned, which is a division of Ser. No. 85,300, Oct. 29, 1970, abandoned, which is a division of Ser. No. 843,230, Jul. 18, 1969, Pat. No. 3,608,604.

[51] Int. Cl.³ .................... C07D 303/34; C07H 15/04; C08F 224/00
[52] U.S. Cl. .............................. 260/348.43; 536/120; 526/273
[58] Field of Search ...................... 260/348 R, 348.43; 536/120; 526/273

[56] References Cited

U.S. PATENT DOCUMENTS

| | | | |
|---|---|---|---|
| 2,752,269 | 6/1956 | Condo et al. | 117/139.4 |
| 3,449,294 | 6/1969 | Danhauser et al. | 260/47 |
| 3,608,604 | 9/1971 | Breslow | 260/348 R |

OTHER PUBLICATIONS

Chemical Abstracts, vol. 67 (1967) 109254v.

*Primary Examiner*—Norma S. Milestone
*Attorney, Agent, or Firm*—Marion C. Staves

[57] ABSTRACT

Disclosed are epoxy-sulfonylazide compounds of the formula

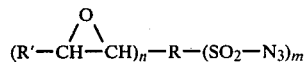

where R is a polyvalent organic radical, R' is a hydrogen, alkyl, cycloalkyl, aryl, or aralkyl radical, and n and m are integers from 1 to 100. Also disclosed is the use of said epoxy-sulfonylazide compounds in modifying polymers, cross-linking polymers, and adhering polymers to certain substrates, e.g., glass and other polymers.

9 Claims, No Drawings

EPOXY-SULFONYLAZIDE COMPOUNDS

This application is a continuation-in-part of my copending application Ser. No. 483,471, filed June 26, 1974, now abandoned, which is in turn a division of my copending patent application Ser. No. 301,003, filed Oct. 26, 1972, now abandoned, which is in turn a division of application Ser. No. 85,300, filed Oct. 29, 1970, now abandoned, which is in turn a division of application Ser. No. 843,230, filed July 18, 1969, now U.S. Pat. No. 3,608,604.

This invention relates to a new class of organic compounds and to their use. More particularly, this invention relates to a new class of epoxy-sulfonylazide compounds and their use in modifying polymers, cross-linking polymers and adhering polymers to certain substrates.

The compounds of this invention are represented by the generic formula

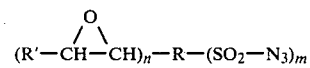

where R is a polyvalent organic radical, R' is a hydrogen, alkyl, cycloalkyl, aryl, or aralkyl radical, and n and m are integers, broadly each being 1 to 100, most preferably from 1 to 10. Generally, R will be an organic radical selected from the group consisting of radicals derived by the removal of two or more hydrogen atoms from alkanes such as, for example, methane, ethane, propane, butane, isobutane, pentane and its isomers, hexane and its isomers, heptane and its isomers, octane and its isomers, nonane and its isomers, decane and its isomers, dodecane and its isomers, hexadecane and its isomers, octadecane and its isomers, and the like; cycloalkanes such as, for example, cyclopropane, cyclobutane, cyclopentane, cyclohexane, cycloheptane, cyclooctane, and the like; alkyl substituted cycloalkanes, such as, for example, propylcyclohexane, pentylcycloheptane, octylcyclohexane, ethylcyclohexane, methylcyclobutane, 1,2-, 1,3- and 1,4-dimethylcyclohexane, 1,2- and 1,3-dimethylcyclopentane, and the like; arenes, such as, for example, benzene, naphthalene, biphenyl, and the like; alkyl substituted arenes, such as, for example, toluene, ethylbenzene, propylbenzene, butylbenzene, hexylbenzene, octylbenzene, 1,2,3-trimethylbenzene, o-, m- and p-xylene, o-, m- and p-diethylbenzene, and the like; alkylenediarylenes, such as, for example, diphenylmethane, 1,2-diphenylethane, 1,4-diphenylbutane, 1,5-diphenylpentane, 1,1-diphenylpropane, 1,3-diphenylpropane, 2,2-diphenylpropane, 1,6-diphenylhexane, 1,8-diphenyloctane, and the like; the alkyloxyalkanes, such as, for example, diethyl ether, dipropyl ether, dihexyl ether, didodecyl ether, dioctadecyl ether, 2,2,2-(methyleneoxymethylene)ethyl, 2,2-bis(allyloxymethylene)-2-methyleneoxymethylene ethyl, propylbutyl ether, and the like; aryloxyarenes, such as, for example, diphenyl ether, and the like; and the foregoing radicals with fluoro, chloro, bromo, or iodo substituents. When an epoxy-sulfonylazide compound of this invention is to be used as a coupling or linking agent for polymers, R preferably is substantially inert to the linking reaction. Typical R' radicals are hydrogen; alkyl, such as, for example, methyl, ethyl, propyl, butyl, isobutyl, pentyl and its isomers, hexyl and its isomers, heptyl and its isomers, octyl and its isomers, nonyl and its isomers, decyl and its isomers, dodecyl and its isomers, hexadecyl and its isomers, octadecyl and its isomers, and the like; cycloalkyl, such as, for example, cyclopropane, cyclobutane, cyclopentane, cyclohexane, cycloheptane, cyclooctane, ethylcyclohexane, metylcyclobutane, and the like; aryl, such as, for example, phenyl, naphthyl, biphenyl, and the like; and aralkyl, such as, for example, benzyl, 2-phenyl ethyl, 3-phenyl propyl, 2-naphthyl ethyl, and the like. In the above described R and R' radicals, the said alkane and alkyl radicals will most preferably contain from 1 to 18 carbon atoms, the said cycloalkane and cycloalkyl radicals will most preferably contain from 3 to 8 carbon atoms and the said arene and aryl radicals will most preferably contain from 1 to 2 carbocyclic rings.

Specific compounds of this invention represented by the foregoing generic formula include but are not limited to:

2,3-epoxypropyl sulfonylazide
2,3-epoxybutyl sulfonylazide
2-chloro-4,5-epoxypentyl sulfonylazide
9,10-epoxyoctadecyl sulfonylazide
2,3-epoxyoctadecyl sulfonylazide
17,18-epoxyoctadecyl sulfonylazide
brominated 9,10-epoxyoctadecyl sulfonylazide containing an average of two bromines
chlorinated 9,10-epoxyoctadecyl sulfonylazide containing an average of two chlorines
fluorinated 9,10-epoxyoctadecyl sulfonylazide containing an average of two fluorines
iodinated 9,10-epoxyoctadecyl sulfonylazide containing an average of two iodines
2,3-epoxypropyl raffinose decasulfonylazide
2,3-epoxypropyl sorbitol pentasulfonylazide
azidosulfonyl-[deca-O-(2,3-epoxypropyl)] raffinose
3-(epoxyethyl)cyclopentyl sulfonylazide
3-(epoxyethyl)cyclobutyl sulfonylazide
2-(epoxyethyl)cyclopropyl sulfonylazide
4-(epoxyethyl)cyclohexyl sulfonylazide
4-(epoxyethyl)cycloheptyl sulfonylazide
4-(epoxyethyl)cyclooctyl sulfonylazide
2,3-dimethyl-4-(epoxyethyl)cyclohexyl sulfonylazide
4-(2,3-epoxypropyl)cyclohexyl sulfonylazide
3-(2,3-epoxypropyl)cyclohexyl-1,5-bis-sulfonylazide
3,5-bis(epoxyethyl)cyclohexyl-sulfonylazide
2,4-bis(epoxyethyl)cyclohexyl-sulfonylazide
3,5-bis(epoxyethyl)cyclooctyl-1,7-bis-sulfonylazide
2,2,2-tris(glycidylmethyl)ethane sulfonylazide having the formula

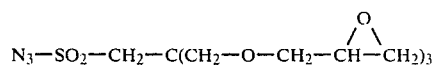

bis(glycidylmethyl)-bis(azidosulfonylmethyl)methane having the formula

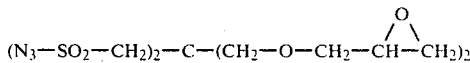

3-glycidyl-2,2-bis(allyloxymethyl)azidosulfonylpropane having the formula

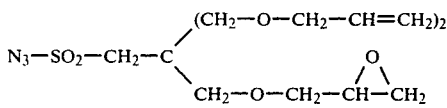

4-(epoxyethyl)-2,5-dichloro-cyclohexyl sulfonylazide
4-(epoxyethyl)benzene sulfonylazide
2,3,5-trichloro-4-(epoxyethyl)benzene sulfonylazide
2,3,5-tribromo-4-(epoxyethyl)benzene sulfonylazide
3,5-bis(epoxyethyl)benzene sulfonylazide
5-(epoxyethyl)benzene-1,3-bis-sulfonylazide
4-(epoxyethyl)phenylethyl sulfonylazide
3-(epoxyethyl)benzyl sulfonylazide
3-cyclohexyl-2,3-epoxypropyl sulfonylazide
4-cyclohexyl-2,3-epoxybutyl sulfonylazide
4-phenyl-2,3-epoxybutyl sulfonylazide
4-(2,3-epoxypropyl)benzene sulfonylazide
3-(2,3-epoxypropyl)benzene sulfonylazide
2-(2,3-epoxypropyl)benzene sulfonylazide
4-(epoxyethyl)naphthalene sulfonylazide
4'-(epoxyethyl)biphenyl-1-sulfonylazide
2,3-dimethyl-4-(epoxyethyl)benzene sulfonylazide
2,3-dimethyl-4-(2,3-epoxypropyl)benzene sulfonylazide
2-ethyl-5-(epoxyethyl)benzene sulfonylazide
4'-(epoxyethyl)diphenylmethane-1-sulfonylazide
3,4-epoxybutyl-2-phenyl sulfonylazide
3-cyclopropyl-2,3-epoxybutyl sulfonylazide
3-cyclooctyl-2,3-epoxybutyl sulfonylazide
3-phenyl-2,3-epoxypropyl sulfonylazide
3-biphenyl-2,3-epoxypropyl sulfonylazide
2-iodo-4-(epoxyethyl)cyclohexyl sulfonylazide
2,3,5,6-tetrafluoro-4-(epoxyethyl)phenyl sulfonylazide
3-bromo-4-(epoxyethyl)benzene sulfonylazide
9,10-epoxydecyl sulfonylazide
9,10-epoxydecyl-2,5-bis-sulfonylazide
2,3-epoxypropyloxypropyl sulfonylazide
2,3-epoxypropyloxyethyl sulfonylazide
4'-(epoxyethyl)phenyloxyphenyl-1-sulfonylazide The copolymer of m-vinylbenzene sulfonylazide and p-vinylstyrene oxide containing approximately 35 sulfonylazide groups and 98 epoxy groups.

The epoxy-sulfonylazides of this invention range from liquids to solids at room temperature and atmospheric pressure and are soluble in chlorinated hydrocarbons, aromatics, acetone, etc. They have a characteristic infrared spectrum with a strong azide peak around 2135 cm$^{-1}$. When heat is applied to the compounds of this invention they decompose giving off nitrogen; as the temperature increases the overall decomposition rate increases. The sulfonyl azide radicals of the compounds readily react with receptive polymers and combine therewith when heated. They also combine with ethylenically unsaturated hydrocarbon groups in a variety of compounds. In so doing, the epoxy portion of the compound remains free and unreacted. While the epoxy portion is heat stable, it readily reacts when contacted with amines or carboxylic acids.

The epoxy-sulfonylazide compounds of this invention can be prepared by various methods. Most preferably these compounds will be prepared by the epoxidation of an unsaturated sulfonylazide compound with peracetic acid or perbenzoic acid. The reaction is usually carried out at a temperature below 100° C. in a solvent. Acetic acid is the most preferred solvent when using peracetic acid but other solvents can be used such as methylene chloride, acetone, ethyl acetate, chloroform, benzene, and the like.

As indicated above, this invention includes the use of the unique epoxy-sulfonylazide compounds in modifying polymers, cross-linking polymers and adhering polymers to certain substrates. All of these uses involve the reaction of the sulfonylazide portion or portions of the epoxy-sulfonylazide compounds with a receptive polymer. In this specification receptive polymer means a polymer having in each polymer chain at least one and generally more than one monomer unit capable of combination reaction with a sulfonylazide radical of a compound of this invention, whereby the residue of the compound is chemically bonded to the polymer. Nearly all polymers are receptive polymers. Preferred examples of a receptive polymer include all types of hydrocarbon polymers including saturated and unsaturated, linear and non-linear, crystalline and amorphous, homopolymers, copolymers, terpolymers, and the like; for example, polyethylene, polypropylene, polystyrene, styrenebutadiene rubber, butyl rubber, natural rubber, polybutadiene, polyisobutylene, ethylene—propylene copolymer, cis-1,4-polyisoprene, ethylene—propylene—dicyclopentadiene terpolymer, and the like; and blends of these polymers with each other and blends of these polymers with organic non-hydrocarbon polymers. In addition to hydrocarbon polymers, preferred examples of a receptive polymer include a large number of organic non-hydrocarbon polymers including homopolymers, copolymers, terpolymers and the like. Typical of these organic non-hydrocarbon polymers are cellulose esters, such as, for example, cellulose acetate-butyrate, cellulose acetate-propionate, cellulose acetate, cellulose propionate, cellulose butyrate, and the like; cellulose ethers, such as, for example, hydroxyethyl cellulose, hydroxypropyl cellulose, and the like; polyesters such as poly(ethylene glycol terephthalate), drying and non-drying alkyd resins and the like; poly(alkylene oxide) polymers, such as poly(ethylene oxide), poly(propylene oxide), poly(ethylene oxide-propylene oxide); polyamides such as nylon, and the like; allyl pentaerythritol derivatives such as, for example, the condensate of triallyl pentaerythritol with diallylidene pentaerythritol, esters of trially pentaerythritol and drying oil fatty acids, and the like; poly(vinyl alkyl ethers) such as, for example, poly(vinyl methyl ether) and the like; poly(vinyl acetals) such as, for example, poly(vinyl butyral) and the like; vinyl chloride polymers having a vinyl chloride content of at least 10 mole percent, such as, for example, poly(vinyl chloride), vinyl chloride—vinyl acetate copolymers, vinyl chloride—vinylidene chloride copolymers, vinyl chloride—fumaric acid copolymers, vinyl chloride—vinyl acetal copolymers, such as, for example, the vinyl chloride—vinyl butyral copolymers, vinyl chloride—vinylidene chloride—acrylonitrile terpolymers, and the like; nitrocellulose, chlorinated natural rubber; sulfochlorinated polyethylene; polysulfide rubber; polyurethane rubber; poly(vinyl acetate); ethylene—vinyl acetate copolymers; poly(vinylidene chloride); vinylidene chloride—acrylonitrile copolymers; ethyl acrylate—2-chloroethyl vinyl ether copolymers; poly(ethyl acrylate); poly(ethyl methacrylate); poly[3,3-bis(chloromethyl)oxetane]; vinyl modified poly(dimethylsiloxane); polychloroprene; butadiene—acrylonitrile copolymers; and the like.

The modified polymers of this invention resulting from the reaction of the sulfonylazide portion or portions of the epoxysulfonylazide compounds with the above receptive polymers are both useful in themselves and necessary intermediates in further modifications of this invention. The amount of epoxy-sulfonylazide compound used to modify a receptive polymer will depend upon the desired end use. In general, however, the amount will be from about 0.01% to about 40% by weight based on the weight of the polymer. The resulting modified polymers are quite stable and generally have physical properties similar to the unmodified polymers. However, the thus modified polymers exhibit new and improved static properties, adhesion properties, launderability, etc. Modification can be carried out by admixing the required amount of epoxysulfonylazide compound with a receptive polymer and heating to a temperature sufficient to react the sulfonylazide portion or portions of the compound with the polymer. In the case of epoxysulfonylazide compounds, this temperature will be in the range of from about 120° C. to about 240°C.

In one modification of this invention, the epoxysulfonylazide compounds are used to bond various polymers to a substrate selected from siliceous materials, metals and other polymers. A typical example of the bonding process of this invention is the bonding of of an α-olefin polymer such as polypropylene to a glass substrate. The said glass substrate, such as glass fibers, glass cloth, plate glass, etc., would first be treated with an amino silane compound. In so doing, the silane portion of the compound would react with the substrate, leaving the amine portion free for later reaction with an epoxy portion of an epoxy-sulfonylazide compound. Next, polypropylene, having been modified with an epoxy-sulfonylazide compound so as to react the sulfonylazide portion with the polymer leaving the epoxy portion free, is placed in contact with the above-described treated glass. The free amine groups on the treated glass react with a free epoxy group on the modified polymer forming a tight bond between the polymer and the glass substrate.

Another typical example of bonding a polymer to a substrate using an epoxy-sulfonylazide compound is the bonding of poly(ethylene terephthalate) tire cord to rubber tire stock. The polyester tire cord is first modified with the epoxy-sulfonylazide compound. In so doing, the sulfonylazide portion or portions react with the polyester leaving the epoxy portion or portions free. Next, the tire cord is generally coated with a conventional tire cord adhesive comprising a mixture of a phenol-aldehyde resin and a rubber terpolymer latex prepared from a vinyl aryl monomer, a diene monomer, and a vinyl pyridine monomer, and then cured. If desired, the coating of conventional tire cord adhesive can be omitted with a proportionate decrease in adhesive strength. Finally, the thus treated tire cord is embedded in a vulcanizable rubber tire stock and cured. While polyester tire cords are mentioned, it will be understood that various other synthetic fibers can be incorporated in rubber tire stock in accordance with this invention. Such other tire cord fibers are, for example, polyolefin, polyamide, polycarbonate, rayon, etc., and mixtures of these fibers. Improved adhesion of the synthetic fibers to the rubber tire stock can be obtained by the process of his invention no matter what the physical form of the fibers, e.g., monofilament, multifilament, twisted, braided, etc. The tire cord can be treated with the epoxy-sulfonylazide compound by any conventional means, for example, by dipping, spraying, brushing or running the cord over a coated roll with a solution of the epoxy-sulfonylazide compound in a suitable liquid. The epoxy-sulfonylazide compound can also be applied as an aqueous suspension, emulsion, or dispersion. After the epoxy-sulfonylazide compound is applied, the cord is heated to a temperature at which the sulfonylazide portion or portions react with the synthetic fiber. Various amounts of the epoxy-sulfonylazide compound can be used. The optimum amount will depend upon the amount of modification desired, the specific epoxy-sulfonylazide compound used, etc. In general, the amount added, based on the cord, will be from about 0.1% to about 10% by weight. As indicated above, the thus modified cord is generally coated with a conventional tire cord adhesive. This adhesive comprises a mixture of (1) a resin, preferably prepared from resorcinol and formaldehyde with (2) a terpolymer latex, which is preferably a styrene—butadiene—vinyl pyridine terpolymer. The vinyl pyridine content of the terpolymer is usually about 5% to about 25%, the styrene content about 5% to about 35%, and the butadiene content from about 50% to about 85%. The latex is applied to the modified tire cord by dipping, spraying, brushing, running the modified cord over a coated roll or other conventional procedure. The amount of latex added will be from about 2% to about 10% based on the weight of the cord. The thus coated cord will be cured at a temperature of from about 190° C. to about 235° C. for a period of time of from about 0.5 to about 2 minutes. The thus treated cord is then embedded in a conventional rubber tire stock and cured under pressure. The vulcanizable tire stocks in which the treated cord can be embedded as a reinforcing medium include natural rubber, and synthetic rubbers such as styrene—butadiene rubbers, ethylene—propylene—diene terpolymer rubbers, polybutadiene, polyisoprene and mixtures and blends thereof with suitable fillers, pigments, antioxidants, and cross-linking (i.e., vulcanizing) agents such as sulfur, peroxides, etc.

Another typical example of bonding a polymer to a substrate using an epoxy-sulfonylazide compound is the bonding of an α-olefin polymer such as polyethylene to a metal substrate. The metal substrate will first be treated with a priming agent. The priming agent is a polyfunctional compound, such as an amino silane compound, which possesses a portion or portions which bond to the metal and another portion or portions which remain free to react with the epoxy group or groups on the epoxy-sulfonylazide compounds. The process of bonding polyethylene to a metal substrate can be carried out in various ways. For example, the substrate can be coated with a solution or suspension of the priming agent, allowed to dry, then coated with a solution or suspension of the epoxy-sulfonylazide compound, allowed to dry and finally contacted with the polyethylene at the decomposition temperature of the azide. By another method, the substrate can be coated with a solution or suspension of the priming agent, allowed to dry, then contacted with a solution or mixture of both the epoxy-sulfonylazide compound and the polyethylene and finally heated to the decomposition temperature of the azide. By still another method the priming agent, epoxy-sulfonylazide compound and polyethylene can be deposited together on the substrate and then heated.

The substrates to which the polymers may be bonded in accordance with this invention include siliceous materials such as glass, asbestos, sand, clay, concrete, stone, brick, ceramic materials, etc.; metals such as aluminum, cadmium, chromium, copper, magnesium, nickel, silver, tin, iron, titanium, zinc, etc., alloys of the metals such as steel, brass, bronze, nickel chrome, etc. and including metals which have been surface treated with phosphates, chromates, etc. or on the surface of which oxides have formed; and other polymers. By the term "other polymers" is meant any polymer other than the polymer to which it is to be bonded. These substrates to which the polymers may be bonded can be in various forms such as sheets, plates, blocks, wires, cloth, fibers, particles, etc.

In another modification of this invention the epoxysulfonylazide compounds are used to cross-link receptive polymers. The polymer to be cross-linked is admixed with from about 0.1% to about 20% by weight of an epoxy-sulfonylazide compound and heated to a temperature sufficient to react the sulfonylazide portion or portions of the compound with the polymer. To effect cross-linking the thus modified polymer is treated with a polyfunctional compound which will react with the free epoxy groups on the polymer. Various polyfunctional compounds can be used to effect the cross-linking, however, most preferred are the polycarboxylic acids and anhydrides such as oxalic acid, phthalic acid, phthalic anhydride, pyromellitic anhydride, etc. and the polyamines, such as m-phenylenediamine; diethylenetriamine, 4,4'-methylenedianiline, etc. When using one of these compounds, the carboxylic acid groups or amino groups react with the free epoxy groups tying together, i.e., cross-linking, the polymer chains.

The following examples will serve to illustrate the invention, all parts and percentages being by weight unless otherwise indicated.

EXAMPLE 1

This example illustrates the preparation of 2,3-epoxypropane-1-sulfonylazide.

To a solution of 14.7 parts of 2-propene-1-sulfonylazide in 105 parts of glacial acetic acid containing one part of sodium acetate was added with stirring at room temperature 40% peracetic acid in an amount in excess of that required to convert the propene radical to an epoxypropane radical. The reaction was stirred at room temperature until the peracetic acid content remained constant and then diluted with 200 parts of water and 135 parts of methylene chloride. The methylene chloride layer was removed and washed with water 5 times and then dried over magnesium sulfate. The methylene chloride solvent was removed leaving 15.1 parts of 2,3-epoxypropane-1-sulfonylazide. The results of an infrared anaylsis of the product for % azido nitrogen and oxirane oxygen is tabulated below:

|  | Found | Calculated |
| --- | --- | --- |
| % $N_3$ | 24.6 | 25.6 |
| % Oxirane oxygen | 9.3 | 9.8 |

EXAMPLE 2

This example illustrates the preparation of 4-(epoxyethyl)benzenesulfonylazide.

To a slurry of 17.5 parts of sodium azide in 20 parts of water and 40 parts of acetone at room temperature was added with rapid stirring a solution of 18 parts of p-styrenesulfonyl chloride in 61 parts of methylene chloride. After stirring at room temperature for 18 hours, the orange-colored reaction mixture was diluted with 150 parts of water and separated. The water layer was re-extracted with 61 parts of methylene chloride and then the combined methylene chloride layers were washed with water and dried over magnesium sulfate. After removal of the methylene chloride solvent 12 parts of the resulting p-styrenesulfonylazide was dissolved in 110 parts of glacial acetic acid containing one part of sodium acetate at 20° C. To the solution was added with agitation 40% peracetic acid in an amount in excess of that required to convert the styrene group to an epoxyethyl benzene group. The reaction was allowed to come to room temperature and stirred until the peracetic acid content remained constant. Then it was diluted with 250 parts of water and 133 parts of methylene chloride. The methylene chloride layer was removed and washed 6 times with water and then dried over sodium sulfate. The methylene chloride solvent was removed to give 12.5 parts of 4-(epoxyethyl)benzenesulfonylazide. The product was analyzed by infrared analysis for azide nitrogen and oxirane oxygen. The results of this analysis are tabulated below:

|  | Found | Calculated |
| --- | --- | --- |
| % $N_3$ | 17.9 | 18.6 |
| % Oxirane oxygen | 6.5 | 7.1 |

EXAMPLE 3

This example illustrates the use of the epoxysulfonylazide of Example 2 in cross-linking polyethylene.

A slurry of 100 parts of high density polyethylene, 0.5 part 4,4'-thio-bis(6-tertiary-butyl-m-cresol) antioxidant and 5 parts 4-(epoxyethyl)benzenesulfonylazide in acetone was prepared. The acetone was removed at 50° C. and the polymer reacted with the epoxy-sulfonylazide by heating at 170° C. for 30 minutes. Ten parts of the thus modified polyethylene was admixed with 0.15 part diethylenetriamine on a two-roll mill and then heated for 30 minutes at 160° C. A control sample of the polymer was treated exactly the same way except for the addition of the epoxy-sulfonylazide compound. The two samples were tested for cross-linking by soaking in decahydronaphthalene at 140° C. The sample containing the epoxy-sulfonylazide was insoluble in the decahydronaphthalene solvent, indicating cross-linking. The control sample, on the other hand, was completely soluble.

EXAMPLE 4

This example illustrates the preparation of a copolymer containing sulfonylazide and epoxy groups and its use.

A mixture of 10 parts of m-vinylbenzene sulfonylazide and 20 parts of p-vinylstyrene oxide is emulsified in 40 parts of water using 0.1 part of dodecyl sodium sulfate surface active agent at room temperature. The emulsion is sparged for one hour with nitrogen gas. To the emulsion is added 0.3 part of ammonium persulfate and 0.3 part of sodium metabisulfite with stirring under an atmosphere of nitrogen. The reaction is exothermic and the temperature of the reaction mixture is allowed to rise to about 35° C. After stirring for 4 hours, the reaction mixture is allowed to cool to room temperature and is then poured into 400 parts of acetone. The copolymer product precipitates, is filtered, washed with acetone and collected. The resulting white powder has a number average molecular weight of approximately 22,000. Analysis for nitrogen and sulfur indicates that the copolymer contains an average of approximately 35 sulfonylazide groups per copolymer molecule. Analysis for epoxide groups indicates that the copolymer contains an average of approximately 98 epoxy groups per copolymer molecule.

A ¼ inch polypropylene sheet is primed with a 10% aqueous emulsion of the above prepared copolymer product. The thus primed sheet is heated at 150° C. for 5 minutes. The primed polypropylene sheet is then coated with a commercial amino resin coating composition and dried at 150° C. for two minutes. The resulting coating was solvent-resistant and exhibited excellent adhesion to the polypropylene sheet.

What I claim and desire to protect by Letters Patent is:

1. An epoxy-sulfonylazide compound having the general formula

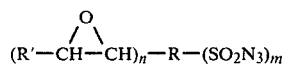

where R is a polyvalent organic radical, R' is a radical selected from the group consisting of hydrogen, alkyl, cycloalkyl, aryl and aralkyl radicals, and n and m are integers from 1 to 100.

2. An epoxy-sulfonylazide compound having the general formula

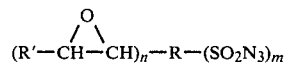

where R is an organic radical selected from the group consisting of radicals derived by the removal of two or more hydrogen atoms from alkanes, cycloalkanes, alkyl substituted cycloalkanes, arenes, alkyl substituted arenes, alkylenediarenes, alkyloxyalkanes, aryloxyarenes, and the foregoing radicals with fluoro, chloro, bromo or iodo substituents, R' is a radical selected from the group consisting of hydrogen, alkyl, cycloalkyl, aryl and aralkyl radicals, and n and m are integers from 1 to 10.

3. An epoxy-sulfonylazide compound having the general formula

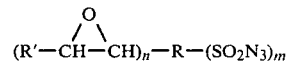

where R is an organic radical selected from the group consisting of radicals derived by the removal of two or more hydrogen atoms from alkanes, cycloalkanes, alkyl substituted cycloalkanes, arenes, alkyl substituted arenes, alkylenediarenes, alkyloxyalkanes, aryloxyarenes, and the foregoing radicals with fluoro, chloro, bromo or iodo substituents, R' is a radical selected from the group consisting of hydrogen, alkyl, cycloalkyl, aryl and aralkyl radicals, and n and m are integers from 1 to 10, said alkane and alkyl radicals containing from 2 to 18 carbon atoms, said cycloalkane and cycloalkyl radicals containing from 3 to 8 carbon atoms, and said arene and aryl radicals containing 1 to 2 carbocyclic rings.

4. 2,3-Epoxypropane-1-sulfonylazide.
5. 4-(Epoxyethyl)benzenesulfonylazide.
6. 9,10-Epoxyoctadecyl sulfonylazide.
7. 2,4-bis(Epoxyethyl)cyclohexyl sulfonylazide.
8. 4-(2,3-Epoxypropyl)benzene sulfonylazide.
9. 2,3-Epoxypropyloxypropyl sulfonylazide.

* * * * *